United States Patent [19]

Nakamura et al.

[11] Patent Number: 5,052,816
[45] Date of Patent: Oct. 1, 1991

[54] JUNCTION INSPECTION METHOD AND APPARATUS FOR ELECTRONIC PARTS

[75] Inventors: Minoru Nakamura; Yasuhiro Oshiro, both of Nakano, Japan

[73] Assignee: Denyo Kabushiki Kaisha, Japan

[21] Appl. No.: 400,009

[22] Filed: Aug. 29, 1989

[51] Int. Cl.⁵ .................. G01N 25/72; G01N 21/71
[52] U.S. Cl. ............................... 374/5; 374/124; 374/137; 228/105
[58] Field of Search ............ 374/4, 5, 124, 7, 137; 228/105

[56] References Cited

U.S. PATENT DOCUMENTS

| | | | |
|---|---|---|---|
| 3,413,474 | 11/1968 | Freeh | 374/7 |
| 4,647,220 | 3/1987 | Adams et al. | 374/5 |
| 4,792,683 | 12/1988 | Chang et al. | 250/341 |
| 4,818,118 | 4/1989 | Bantel et al. | 374/7 |
| 4,854,724 | 8/1989 | Adams et al. | 374/5 |
| 4,941,256 | 7/1990 | Capson et al. | 29/833 |

FOREIGN PATENT DOCUMENTS

| | | | |
|---|---|---|---|
| 126339 | 6/1987 | Japan | 374/4 |
| 305238 | 12/1988 | Japan | 374/5 |

OTHER PUBLICATIONS

R. Vanzetti et al., "Laser Inspection of Solder Joints" Conference: CECON 80, 1980 Cleveland Electrical/Electronics Conference, Cleveland, Ohio, USA (20-22 May 1980), pp. 103-108.

Sechi et al., "Computer-Controlled Infrared, Microscope for Thermal Analysis of Microwave Transistors", 1977 IEEE MTT S International Microwave Symposium Diget, pp. 143-146.

McLaughlin et al., "Non-Destructive Examination of Fibre Composite NDT International", Apr. 1980, pp. 56-62.

*Primary Examiner*—William A. Cuchlinski, Jr.
*Assistant Examiner*—W. Morris Worth
*Attorney, Agent, or Firm*—Stevens, Davis, Miller & Mosher

[57] ABSTRACT

A plurality of lead wires such as those from an IC (an integrated circuit) is irradiated by a fan beam at same time. Infrared rays radiated from the portion which is irradiated by the fan beam and the periphery of the portion are detected so as to catch a thermogram exhibiting the temperature distribution. The thermogram is processed by image processing so as to produce a temperature distribution image. This image is visually compared with a standard temperature distribution-pattern on a display apparatus to judge whether soldering on those lead wires is defective or not.

3 Claims, 5 Drawing Sheets

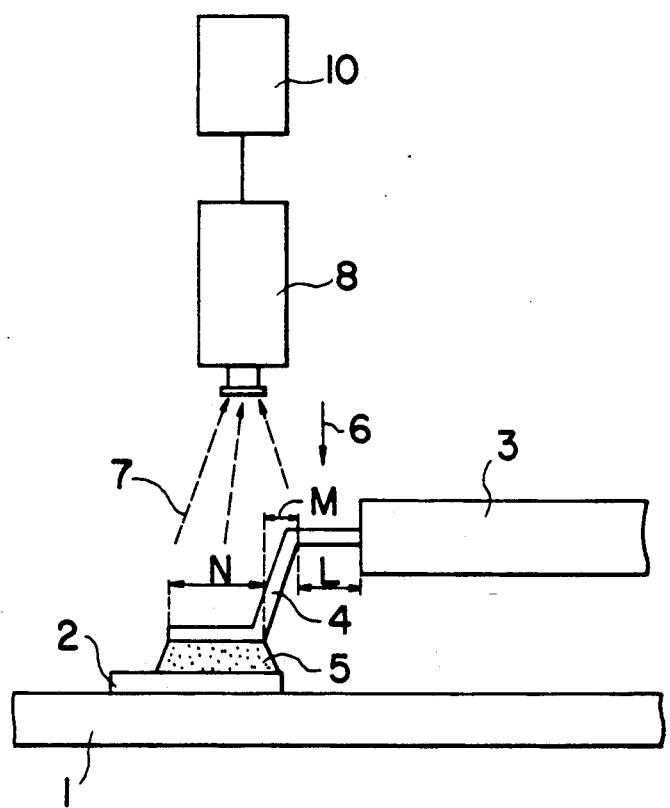
F I G. 1
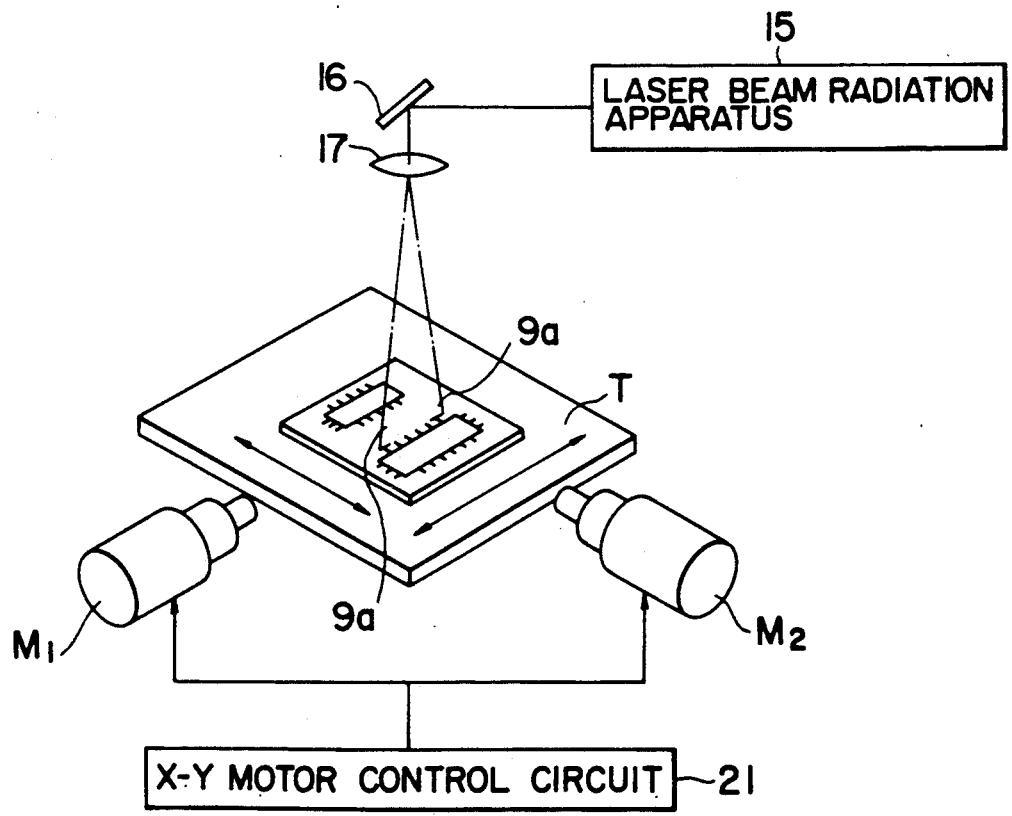
F I G. 3

JUNCTION INSPECTION METHOD AND APPARATUS FOR ELECTRONIC PARTS

BACKGROUND OF THE INVENTION

The present invention relates to a junction inspection method for electronic parts, particularly to an inspection methods for electronic circuit boards in which the soldering condition of the soldered portions is inspected through its temperature distribution.

Junctions of electronic parts such as the soldered portions of electronic circuit boards often have defects, and several kinds of junction inspection methods have already been proposed. For example, whether soldering is nondefective or not is judged by visual inspection to examine if solder is distributed in adequate shape to the portion to be soldered. Japanese patent laid-open No. 59-202048 entitled "ELECTRONIC PARTS-CONNECTED STATE INSPECTION METHOD" discloses a method involving measuring charges in temperature increases per unit time due to infrared rays radiated from conductive patterns when an energy beam is irradiated on lead wires of electronic parts connected to conductive patterns on a circuit board and determining that the soldering is defective if the measured data are large and is nondefective if the data are small.

Furthermore, Japanese patent laid-open No. 61-241641 entitled "SOLDERING INSPECTION APPARATUS" discloses the apparatus for inspecting the soldered portions of flat package type integrated circuits to determine if the soldered portions are nondefective or not by measuring the temperature increase per unit time of the soldered portions by heating the terminals of the integrated circuits and comparing the temperature increase with that premeasured for nondefective soldered portions.

Both Japanese patent laid-open Nos. 59-202048 and 61-241641 disclose a method to determine if soldered portions are nondefective or not by measuring the amount of solder attached to the junctions of electronic parts being judged for nondefectiveness of the soldered portions, on the basis of the temperature increase-change per unit time of the soldered portions. It is very hard to determine if the soldering is nondetective or not by visually inspecting the soldering state and this often causes inaccurate judgements.

Microminiaturization and high precision are being required for electronic circuit boards in recent years and the conventional methods of inspection based on the temperature increase-change per unit time on a point of a soldered portion or inspection of the amount of solder only cannot provide sufficient inspection in that it is difficult to detect defects such as blow holes or pin holes formed in soldered portions or bridges formed over adjoining junctions, for example.

SUMMARY OF THE INVENTION

It is, accordingly, an object of the present invention to provide a junction inspection method and apparatus for electronic parts to determine the defectiveness of soldering on junctions by measuring relative phenomenon of heat transfer on a plurality of junctions as a surface. This method is different from the conventional method of determining the defects of soldered portions by detecting the temperature increase-change per unit time on a point of a junction.

Briefly, the present invention comprises the inspection method to determine if junctions are nondefective or not in such a manner that the portions to be measured are junctions including heat transferring material and irradiated by heat energy, where the infrared rays radiated from the portions are received by an infrared ray photographic means to catch a thermogram. The thermogram exhibiting the temperature distribution of the portions is processed by image processing into a temperature distribution-image which is compared with a standard temperature distribution-pattern.

In the present invention, when the junctions of an electronic part forming the object to be measured are irradiated by heat energy, the infrared rays radiated from the junctions are received by the infrared ray photographic means to catch the thermogram. The thermogram exhibiting temperature distribution of the junctions is processed by image processing to produce an image which clearly shows perfectly joined portions and imperfectly joined portions of the junctions.

It is, therefore, easy to determine if the object to be measured is nondefective or not by comparing this image with the standard temperature-pattern which is preprocessed by image processing.

BRIEF DESCRIPTION OF THE DRAWINGS

FIG. 1 shows an inspection means suggesting the operational principle of the present invention, FIG. 3 shows the junctions of an IC (integrated circuit) irradiated by heat energy.

DESCRIPTION OF THE PREFERRED EMBODIMENT

Figure 2:
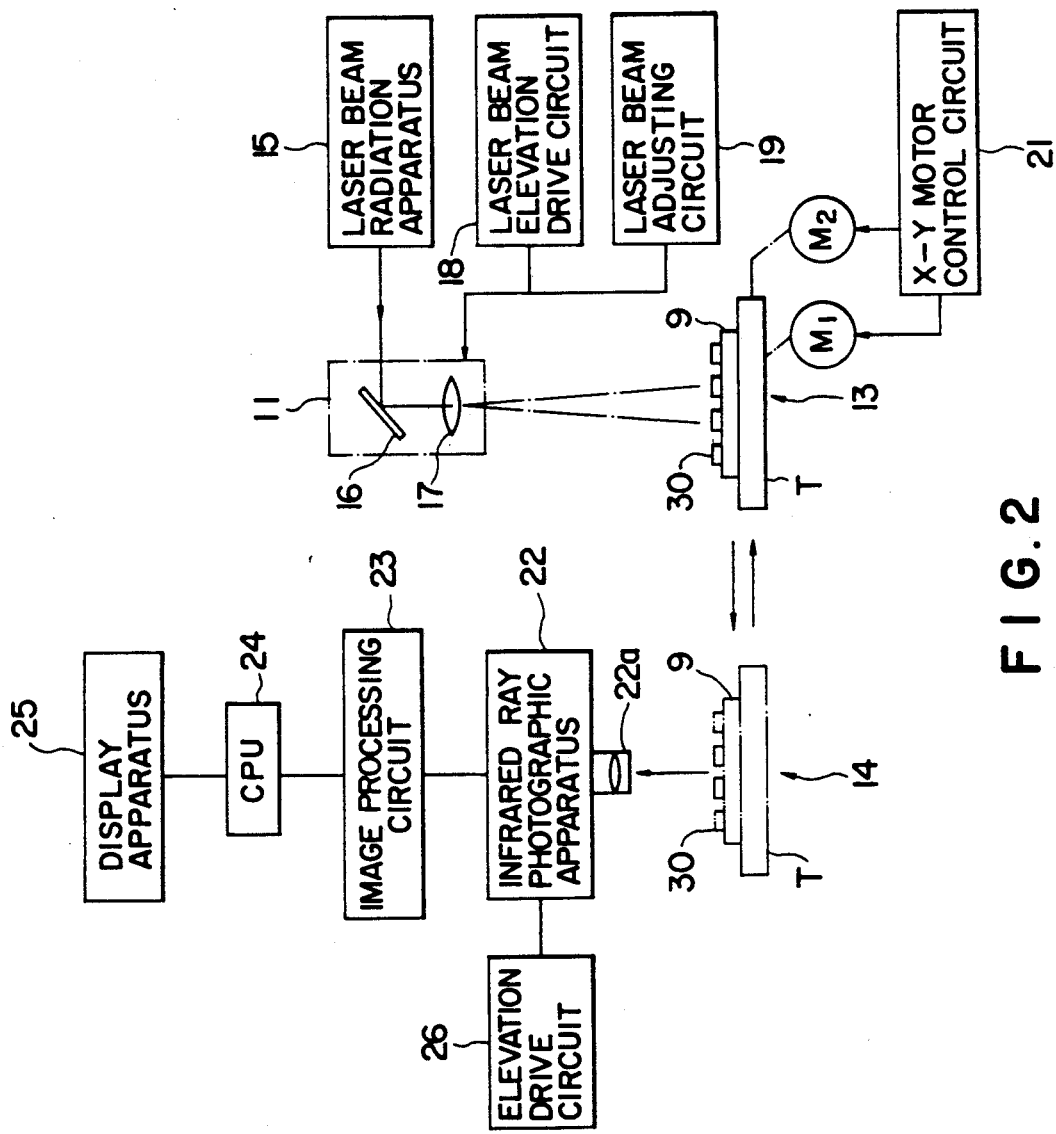
FIG. 2 shows a schematic diagram of the preferred embodiment of the present invention.

A preferred embodiment of the present invention will now be explained below. The operational principle of the present invention will be explained before the explanation of the preferred embodiment. The junctions of electronic parts subjected to the present invention are the portions joined to the circuit board by such means as soldering.

FIG. 1 shows inspection means suggesting the principle of operation of the present invention for one of object of measurement in the electronic part.

In the figure, numeral 1 denotes a printed-circuit board and 2 denotes a conductive pattern on the printed-circuit board 1. A lead wire 4 of an IC 3 as an electronic part is soldered to the conductive pattern 2 through a soldered portion 5. An energy beam 6 such as a laser beam is irradiated to the lead wire 4 of the IC 3. Infrared rays 7 radiated from the measured portion, irradiated by heat energy, that is, the lead wire 4 and the soldered portion 5 are received by an infrared ray photographic means 8 to catch a thermogram. The thermogram exhibiting the temperature distribution of the object to be measured is displayed on a display means 10.

It is, by aforementioned procedure, possible to detect whether the soldering state cf the object is adequate or not. L, M and N shown in FIG. 1 will be explained later.

FIG. 2 shows a schematic diagram of the preferred embodiment of the present invention. In the figure, a soldered electric circuit board 9 is, as is shown in FIG. 3, arranged on a X—Y table T which transfers the electric circuit board 9 in the X—Y direction, by controlling two motors $M_1$ and $M_2$ by a X—Y motor control circuit 21.

In a heating station 13, a laser beam radiated from a laser beam radiation apparatus 15 is transformed into a fan beam by a lens 17 through a mirror 16. A plurality of lead wires 9a—9a of an IC 30 to be measured on the electric circuit board 9 is irradiated by the fan beam at the same time. A laser beam adjusting circuit 19 makes it possible to heat the object to be measured in the direction of a right angle and turn an optical system 11 consisting the mirror 16 and the lens 17 in a right angle in the case of irradiating lead wires of the IC 30 in the side of the right angle. A laser beam elevation drive circuit 18 keeps the optical system 11 away from the electric circuit board 9 so as to increase the number of the lead wires 9a—9a of the IC 30 to be heated or vice versa. The X—Y motor control circuit 21, by operation of the X—Y table T, after heating operation, transfers the heated electric circuit board 9 into a photographing station 14 indicated by an arrow and illustrated by imaginary lines or vice versa.

In the photographing station 14, as is shown in FIG. 2, an infrared ray photographic apparatus 22 scans at a high speed and photographs all heated lead wires 9a—9a of the soldered electric circuit board 9 to produce image signals corresponding to the temperature distribution and send the image signals to an image processing circuit 23. The image processing circuit 23 converts the image signals exhibiting the temperature changing condition into binary signals and sends the binary signals to a CPU 24. By command from the CPU 24, a display apparatus 25 displays temperature distribution-state on all heated lead wires 9a—9a of the soldered IC 30. The temperature distribution-image displayed on the display apparatus 25 is compared with a prepared standard temperature distribution-pattern by visual inspection to determine whether the soldering is nondefective or not. Conventional methods may be used as other methods for this comparison. For example, a standard temperature distribution-pattern is previously processed by image processing and stored in a memory of a computer, and is then displayed on a part of the screen of the display apparatus 25 on which the measured temperature distribution-image is being displayed, so as to enable visual comparison. Numeral 26 denotes an elevation drive circuit for the infrared ray photographic apparatus 22.

The X—Y motor control circuit 21 is a transfer means for irradiating the plurality of the lead wires 9a—9a of the IC 30 by the laser beam radiated from the laser beam radiation apparatus 15 and transformed into the fan beam through the mirror 16 and the lens 17 and also for photographing the temperature distribution-state of the lead wires 9a—9a of the IC 30 by a lens 22a attached to the infrared ray photographic apparatus 22.

Figure 4A:
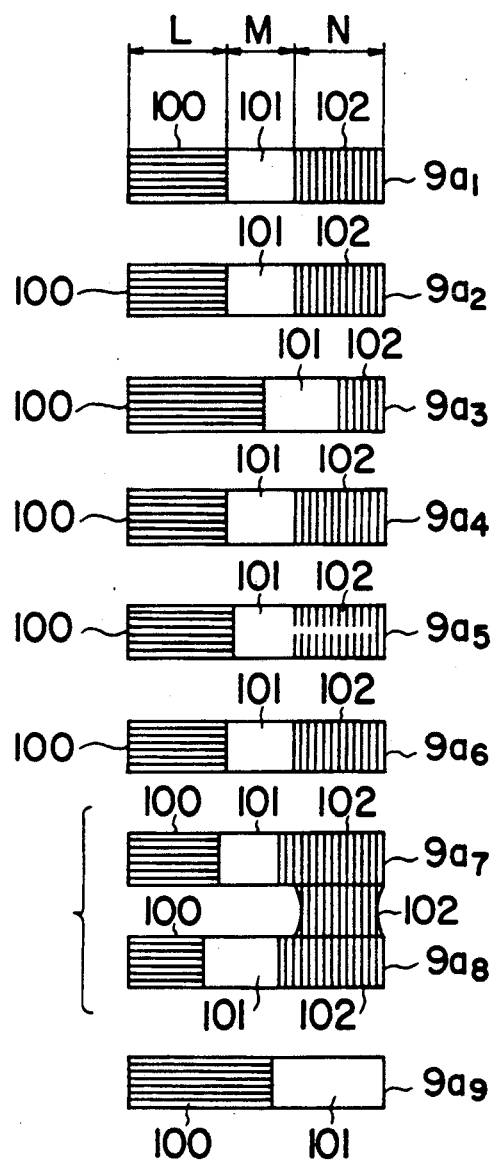
FIG. 4A shows a schematic view of a temperature distribution-image of a measured object as displayed on a display means.
Figure 5:
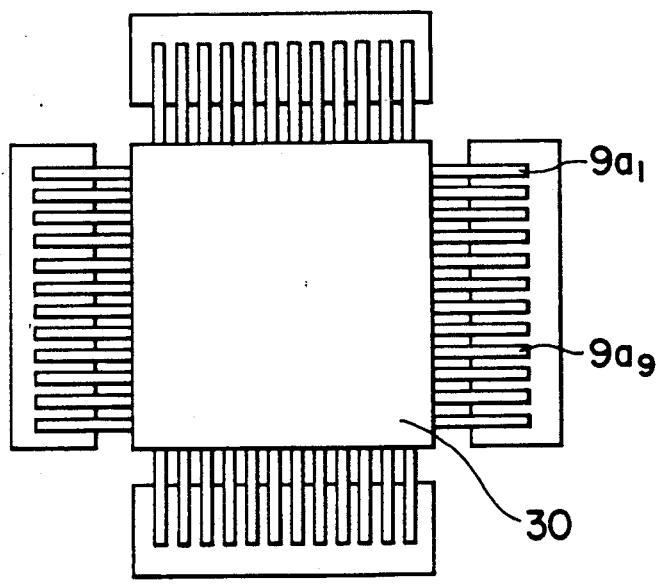
FIG. 5 shows the junctions of the IC to be measured.

FIG. 4A shows a schematic view of the temperature distribution image of the object to be measured, as displayed on the display apparatus 25 and particularly shows the temperature distribution of the heated lead wires $9a_1$—$9a_9$ of the soldered electric circuit board 9 shown in FIG. 5.

In FIG. 4A, the portions 100, 101 and 102 are displayed on the screen of the display apparatus 25 in red, yellow and blue, respectively, while the area L indicates the portion of the object to be heated, the area N indicates the soldered portion of the object and the area M indicates the lead wire between the portion of the object to be heated and the soldered portion of the object and correspond to L, M and N shown in FIG. 1, respectively.

By these displays, the soldering is determined to be nondefective in the junctions of the lead wires $9a_1$, $9a_2$, $9a_4$ and $9a_6$, insufficient in the junction of the lead wire $9a_3$, having a blow hole in $9a_5$, having a bridge formed over $9a_7$ and $9a_8$ and having solder peeling off in $9a_9$.

Figure 4B:
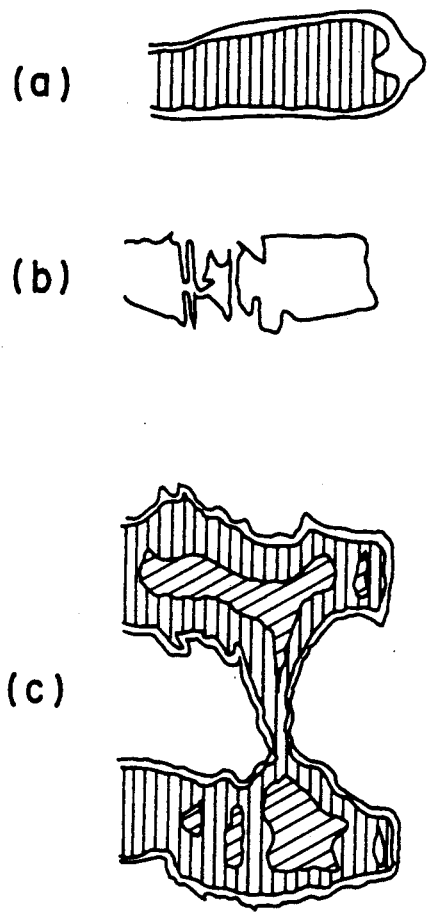
FIG. 4B shows a sketch of an image which is actually observed, displayed on the display means and printed out. In the figures, (a) shows the case of perfect soldering, (b) shows the case of imperfect soldering and (c) shows the case of the existence of a bridge.

FIG. 4B shows a sketch of the image which is actually observed, displayed on the display apparatus 25 and printed out. This sketch shows the area N of the soldered lead wire. In the figure, (a) indicates nondefective soldering, (b) indicates insufficient soldering and (c) indicates a bridge, on the other hand, in the temperature distribution images, "noncolored", "||||" and "////" indicate "high", "middle" and "low" temperatures, respectively.

The aforementioned embodiment of the present invention discloses a method to inspect soldering state from the surface side of the electric circuit board. However, when electronic parts are soldered to the back side of the electric circuit board via through-holes or the like, it is possible to inspect the soldering state from the back side of the electric circuit board.

The present invention discloses such a method that an object to be measured, such as an electronic part, is irradiated by heat energy, an infrared ray photographic means photographs infrared rays radiated from the object to be measured and the temperature distribution obtained from this procedure is processed by image processing and displayed on such as a CRT for comparison with a standard temperature distribution-image which is previously processed by image processing to determine whether the object is nondefective or not. The method of the present invention does not catch the temperature changing per unit time as is disclosed in conventional methods, but catches defective portions of the object as surfaces and not points by using a heat-transfer-phenomenon in the periphery of the portions to be measured to produce a temperature distribution-image, and then determine whether the object is nondefective or not by comparing said image with a standard temperature distribution-image. Accordingly, no special skill is required and consistently accurate inspection can be performed.

According to the present invention, whether soldering is defective or not is not judged by parameters such as the amount of solder but rather by catching the solder as a surface, so that a defective phenomenon, such as blow holes or pin holes in soldered portions, are clearly transformed into images and a phenomenon that a bridge is formed because soldered portions join each other in an integrated circuit is observed on the basis of the heat transfer state at the periphery of the object to be measured. Those phenomena, accordingly, are detected easily and highly accurate inspection can be speedy performed, so that aforementioned method and apparatus are greatly useful in the field of the present invention.

What is claimed is:

1. An apparatus for inspecting soldered junctions of an electronic part having a plurality of terminals to be measured said apparatus comprising:
   (a) a heating station which includes:
      generating means for generating a heat energy fan beam directed toward the soldered junctions to be inspected; and
      irradiating means, having an adjusting means for adjusting the width of the fan beam from said generating means, for irradiating the soldered junctions with the fan beam;
   (b) a photographing station which includes:
      detecting means for detecting infrared rays radiated from the soldered junctions after irradiation by the fan beam at said heating station so as to produce a signal representing the condition of the soldered junctions; and
      image processing means for processing the signal from the detecting means so as to make up data to be used for displaying the condition of the soldered junctions; and
   (c) transferring means for transferring the electronic part between the heating station and the photographing station.

2. The apparatus of claim 1, wherein said adjusting means has means for varying the distance from said adjusting means to the soldered junctions.

3. The apparatus of claim 1, wherein said adjusting means has means for varying the angle of the fan beam.

* * * * *